United States Patent [19]
Hansson et al.

[11] Patent Number: 5,656,605
[45] Date of Patent: Aug. 12, 1997

[54] DEVICE TO PROMOTE DRUG-INDUCED NERVE REGENERATION

[75] Inventors: Hans-Arne Hansson, Hovas, Sweden; Michael R. Wells, Boylston, Mass.; Samuel E. Lynch, Grafton, Mass.; Harry N. Antoniades, Newton, Mass.

[73] Assignee: Institute of Molecular Biology, Inc., Worcester, Mass.

[21] Appl. No.: 187,210

[22] Filed: Jan. 26, 1994

[51] Int. Cl.⁶ .............................. A61B 17/08; A61K 9/00; A61K 38/18; A61L 31/00
[52] U.S. Cl. ..................... 514/21; 424/93.21; 424/93.7; 424/423; 424/426; 604/890.1; 606/152
[58] Field of Search .................................... 514/2, 12, 21; 604/890.1; 424/423, 426, 93.2, 93.21, 93.7; 623/12; 606/152

[56] References Cited

U.S. PATENT DOCUMENTS

| | | | |
|---|---|---|---|
| 4,778,467 | 10/1988 | Stensaas et al. | 623/12 |
| 4,878,913 | 11/1989 | Aebischer | 623/12 |
| 5,092,871 | 3/1992 | Aebischer et al. | 606/152 |
| 5,147,399 | 9/1992 | Dellon et al. | 623/12 |
| 5,292,802 | 3/1994 | Rhee et al. | 424/422 |

FOREIGN PATENT DOCUMENTS

| | | |
|---|---|---|
| 02468 | 3/1989 | WIPO . |
| WO93/02695 | 2/1993 | WIPO . |

OTHER PUBLICATIONS

Experimental Neurology, vol. 107, No. 1, issued Jan. 1990, Kosaka, "Enhancement of Rat Peripheral Nerve Regeneration . . . ", pp. 69–77.
Experimental Neurology, vol. 95, issued 1987, Madison et al, "Peripheral Nerve Regeneration with Entubulation Repair . . . ", pp. 378–390.
Journal of Neurosurgery, vol. III, No. 1, issued Jan. 1946, Weiss et al, "Guides For Nerve Regeneration Across Gaps", pp. 375–389.
Aebischer et al., "Basic Fibroblast Growth Factor Released From Synthetic Guidance Channels Facilitates Peripheral Nerve Regeneration Across Long Nerve Gaps" J. Neuroscience Res., 23:282–289, 1989.
Alexander et al., "Further Experiments on Bridging of Long Nerve Gaps in Monkeys" Proc. Soc. Exp. Biol. Med., 68: 380–382, 1948.
Chen et al., "Facial Nerve Regeneration in the Silicone Chamber: The Influence of Nerve Growth Factor" Experimental Neurology, 103: 52–60, 1989.
Lundborg et al., "Regeneration of peripheral nerve through a preformed tissue space. Preliminary observations on the reorganization of regenerating nerve fibres & perineurium" Brain Research, 178: 573–576, 1979.
Lundborg et al., "Nerve regeneration through preformed pseudosynovial tubes" J. Hand Surgery, 5: 35–38, 1980.
Rich et al., "Nerve Growth Factor Enhances Regeneration through Silicone Chambers" Experimental Neurology, 105: 162–170, 1989.
Sjöberg et al., "Insulin–like growth factor (IGF–1) as a stimulator of regeneration in the freeze–injured rat sciatic nerve" Brain Research, 485: 102–108, 1989.
Stopford, "The Treatment of Large Defects in Peripheral Nerve Injuries" The Lancelet, CXCIX: 1296–1297, 1920.
Valentini et al., "Collagen–and Laminin–Containing Gels Impede Peripheral Nerve Regeneration through Semipermeable Nerve Guidance Channels" Experimental Neurology, 98: 350–356, 1987.

*Primary Examiner*—Jeffrey E. Russel
*Attorney, Agent, or Firm*—Clark & Elbing LLP

[57] ABSTRACT

The invention relates generally to a system for promoting regeneration of a damaged nerve. In particular, the invention comprises: (1) a guide tube constructed to be attached to the damaged nerve; (2) guiding filaments disposed within the guide tube; and, (3) a therapeutic composition enclosed by the guide tube. Both the guide tube and the guiding filaments are composed of biologically compatible materials, while the therapeutic composition contains a nerve-growth-stimulating agent dispersed in a matrix-forming material. During treatment, the guide tube is inserted between the ends of lesioned nerves, resulting in the stimulation of axon growth.

4 Claims, 3 Drawing Sheets

DEVICE TO PROMOTE DRUG-INDUCED NERVE REGENERATION

The invention relates generally to a system for promoting regeneration of a damaged nerve. In particular, the invention comprises: (1) a guide tube constructed to be attached to the damaged nerve; (2) guiding filaments disposed within the guide tube; and, (3) a therapeutic composition enclosed by the guide tube. Both the guide tube and the guiding filaments are composed of biologically compatible materials, while the therapeutic composition contains a nerve growth-stimulating agent(s) placed within or otherwise delivered to the guide tube lumen. During treatment, the device is inserted between the ends of lesioned nerves, resulting in the stimulation of axon growth.

BACKGROUND OF THE INVENTION

Recent experiments have used entubation of damaged nerves as a method for assessing the potential of nerve regenerative agents (Lundborg et al., Brain Res. 178: 573–576 (1979); Lundborg et al., J. Hand Surg. 5: 35–38, (1980)). In the models discussed in these references, the two ends of the damaged nerve are inserted and sutured into a pseudomesothelial-lined guide tube which is kept open by a stainless steel thread. Similar experiments (utilizing other materials for guide tubes) have demonstrated how the guide tube can substantially increase the distance over which damaged nerve tissue can be regenerated (Seckel, Muscle and Nerve 13: 785–800, (1990); Varon and Williams Peripheral Nerve Rep. Regen 1: 9–25, (1986); Williams et al. in *Neurology and Neurobiology. The Current Status of Peripheral Nerve Regeneration*, Gordon et al. eds.: 111–122 (1988); MacKinnon and Dellon, *Surgery of the Peripheral Nerve*: 561–572, (1988)). In the experiments described in these references, the regeneration of the nerve was shown to be enhanced by the presence of guide tubes, which resulted in an increase in the size of regenerating axons and a decrease in the time required for the regenerating nerve to bridge the damaged region.

The introduction of matrix-forming materials within the guide tube lumen has also been shown to have influences on nerve regeneration. Some of the substances which have shown some effect include collagen (Cordeiro et al. Plast. Reconstr. Surg., 88: 1013–1020), laminin (Madison et al. Exp. Neurol. 88: 767–772, (1985)) and fibrin clots (Williams et al. in *Neurology and Neurobiology. The Current Status of Peripheral Nerve Regeneration*, Gordon et al. eds.: 111–122 (1988); Williams and Varon, J. Comp. Neurol. 231: 209–220). In vitro experiments have also indicated that other matrix-forming materials, or materials attached to the guide tube surface, may enhance neuron outgrowth (Bailey et al. J. Neurocytol. 22: 176–184 (1993); Seckel, Muscle and Nerve 13: 785–800 (1990)).

The use of entubation repair for performing nerve grafts is also advantageous because the guide tube can be filled with materials containing growth factors which can potentially enhance nerve regeneration or improve certain characteristics of the regenerated axons. These improvements include increases in axon size and facilitation of myelin maturity, as well as increases in axon numbers. Some of the compounds which have shown some efficacy when applied to the peripheral nervous system either directly or systemically are listed in Table 1 of Seckel, Muscle and Nerve 13: 785–800, (1990). In particular, nerve-growth-stimulating agents which have been applied to injured nerves using a guide tube or nerve chamber include nerve growth factor (Rich et al. Exp. Neurol. 105: 162–170, (1989); Chen et al. Exp. Neurol. 103: 52–60, (1989)), fibroblast growth factor (Cordeiro et al. Plast. Reconstr. Surg. 83: 1013–1019, Seckel, Muscle and Nerve 13: 785–800, (1990)), insulin-like growth factor-1 (Nachemson et al., Growth Factors 3: 309–314, (1990); Sjoberg and Kanje, Brain Res. 485, 102–108, ACTH (Horowitz, Muscle & Nerve 120: 314–322, and a mixture of laminin, testosterone, GM-1 and catalase (Miller et al. Brain Res. 413: 320–326 (1987)). Growth factors and other agents have also been incorporated directly into guiding tubes made from resorbable or noresorbable polymers to allow a slow release of the growth factor over time (Aebischer et al., J. Neurosci. Res. 23: 282–289 (1989); Guenard et al. J. Neurosci. Res. 29: 396–400, (1991)).

Guiding filaments, usually consisting of threads of suture material, have also been used with limited success for the repair of damaged nerves (Alexander et al., Proc. Soc. Exp. Biol. Med. 68: 380–383, (1948); Stopford, Lancet, 1296–1297, (1920)). Despite these efforts, the use of guide materials to facilitate the growth of injured nerves has been largely abandoned in favor of nerve grafts. Experimentally, guiding filaments have been made of materials including laminin (Madison, et al., Exp. Neurol. 95: 378–390, (1987)), fibronectin (Knoops et al. Brain Res. Bull. 30: 433–437, (1993)), collagen (Valentini et al. Exp. Neurol. 98: 350–356, (1987)), carbon fibers (Khan et al., Brain Res 541: 139–145, (1991)) and coated filament materials (Yoshi et al. Exp. Neurol 96: 469–473). The use of these, and other materials, has been reviewed previously (Seckel, Muscle and Nerve 13: 785–800, (1990)).

While the use of entubation for the repair of damaged nerves has shown some promise, detracting factors, including possible inflammation or compression of the nerve, have led some experts in the field to conclude that the only damaged regions successfully bridged by entubation techniques were those which could be more appropriately closed using an end-to-end suture (Sunderland, *Peripheral Nerve Injuries and Their Repair*, p. 605 (1978)).

SUMMARY OF THE INVENTION

The invention features a system which can be used to bridge either large (greater than 10 mm) or small (between 0.5 mm and 10 mm) gaps in injured nerves. The system of the invention includes an encasing structure, i.e., a guide tube having a longitudinal axis; guiding filaments running generally parallel to the longitudial axis of the guide tube; and, a therapeutic composition placed within or otherwise delivered to the guide tube lumen. The unique feature of the invention is embodied in the combination of all of these elements to form a device to enhance the regeneration of injured nerves.

In preferred embodiments, both the guide tube and the guiding filaments are made of a biologically inert polymer such as polyglycolic acid; the therapeutic composition includes a biocompatable carrier substance such as methylcellulose gel and a nerve-growth-stimulating agent such as platelet-derived growth factor, insulin-like growth factor-I, insulin-like growth factor-II, nerve growth factor, or whole cells, preferably Schwann cells. (Platelet-derived growth factor, or PDGF, refers to the naturally occurring heterodimer, as well as to A or B-chain homodimers, which are commercially available.)

Other nerve-growth-stimulating agents include acidic fibroblast growth factor, basic fibroblast growth factor, transforming growth factor-α, transforming growth factor-β, brain-derived neurotropic factors, ciliary neurotropic factor, glial growth factors, and related compounds. Other whole cells which can be used include endothelial cells, fibroblasts, and genetically altered cells, which express one or more of the above-mentioned nerve stimulating compound.

"Inert polymeric materials", as used herein, refer to collagen-based materials, silicone, polyglucuronic acid, polylactic acid, polytetraethylene, Silastic™, poly-n-acetylglucosamine, ethylene-vinyl acetate, and related materials. In preferred embodiments, silicone rubber (Silastic™) or a biocompatable resorbable material, preferably polyglycolic acid or polylactic acid or copolymers thereof is used to make the guide tube.

Preferably, the guide filaments also consist of an inert polymeric material, preferably a biocompatable resorbable material. In preferred embodiments, the guide filaments comprise polylactic or polyglycolic acid or mixtures thereof.

The carrier substance preferably consists of a biocompatable matrix-forming material. "Biocompatable matrix-forming materials", as used herein, refer to collagen, methylcellulose gel, fibrin and other blood-derived proteins, Matrigel™, Biomatrix I™, and related materials into which the therapeutic agent can be admixed.

DESCRIPTION OF THE PREFERRED EMBODIMENTS

Figure 1:
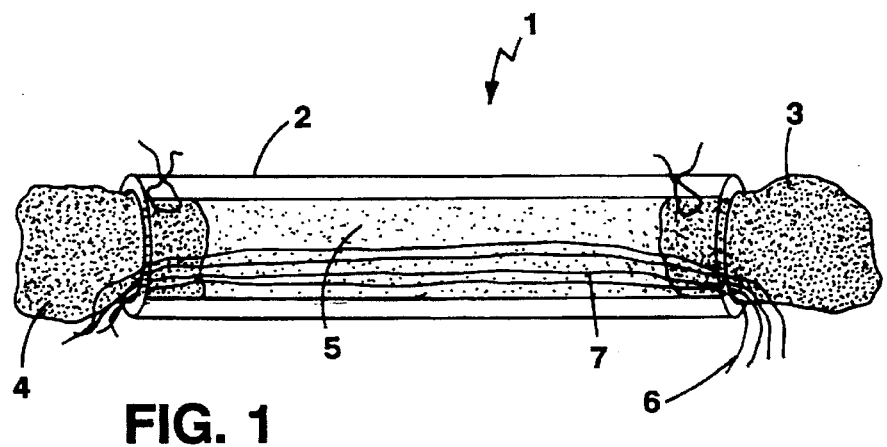
FIG. 1 shows an illustration of the present invention.

Referring to FIG. 1, the proximal end 4 and distal end 3 of the injured nerve are inserted into the guide tube 2, and are held in place by sutures or by other suitable means. While FIG. 1 shows the injured nerve extending only a short distance into the device 1, both proximal and distal ends of the nerve may also be covered by longer lengths of the guide tube 2. This distance may extend up to the point where division of nerve fascicles at the distal end 3 prevents further encasement. A matrix-forming material 5 containing a nerve-growth-stimulating agent(s) is enclosed by the guide tube. The guiding filaments 6 are typically applied prior to the nerve repair as a loop extending through the lumen of the guide tube 7 and around the outside of the guide tube. The segment of the loop outside the guide tube is then cut away when the repair is completed. The construction of the guide tube may be varied to contain isolated longitudinal divisions, with guide filaments in each division facilitating the separation of regenerating fascicles within the nerve. In this particular embodiment, the longitudinal divisions act as a separate guide for each fascicle, with the entire device being essentially comprised of smaller individual devices of similar construction.

The device as a whole is intended to be a simultaneous nerve guide and therapeutic agent delivery system as distinguished from nerve guide tubes alone or delivery techniques presently in the public domain. The unique features of the device are the use of guiding filaments in conjunction with a tubular structure and matrix containing a nerve stimulating substance(s), most preferably growth factors. The guiding filaments facilitate the formation of a pathway upon which cells from both stumps of the injured nerve may migrate out and form a "cable" of regenerating axons. Experimental evidence has indicated that guide tubes comprising guide filaments in the presence of therapeutic agents exhibit an improvement in the regeneration of axons when compared to devices comprising a tube and matrix alone, a tube and filaments alone, filaments and matrix alone, or a tube, filaments and matrix alone. The guide tube may consist of either resorbable or nonresorbable (most preferable resorbable) material which may be permeable or impermeable to materials soluble in aqueous solutions. Materials of which the guide tube may be constructed include, but are not limited to, collagen complexes, polylactic acid, polyglycolic acid, permselective polytetraethylene, Silastic™, poly-n-acetylglucosamine, or polymers into which growth factors may be incorporated directly (e.g. ethylene-vinyl acetate).

The guide thread filament materials may consist of biocompatable materials similar or identical to the materials used for the guide tube. Other materials that may be used include presently available suture materials, such as Vicryl™, gut, nylon, poly-n-acetylglucosamine, and other materials which can act as a compatible substrate for the formation of a cable of regenerating axons.

The materials used for carrier matrices in the present invention include any material or system in which therapeutic agents can be inserted into or conveyed into the lumen of the device for delivery to the injured nerve within the confines of the guide tube, and include any biocompatible material into which growth factors or other therapeutic agents can be suspended or dissolved. Such carrier materials may include, but are not limited to, collagen, methylcellulose gel, fibrin or other blood derived proteins, extracellular matrix materials such a Matrigel™ (Collaborative Research, Inc., Waltham, Mass.) Biomatrix 1™ (Biomedical Technologies, Inc., Stoughton, Mass.) or other related materials. The carrier may also comprise saline, water or other buffers which may be delivered to the device at the time of device insertion using a continuous delivery system, such as an osmotic mini-pump or externally accessible catheter placed at the distal end of the device for continuous delivery. Genetically altered or unaltered cells capable of delivering nerve-growth-stimulating agents may also be incorporated as a delivery system to the injured nerve within the guide tube.

Nerve-growth-stimulating agents to be placed within the device include neurotrophic, chemotactic, mitogenic, or similar substances, or combinations or mixtures thereof, which are capable of stimulating axonal growth directly or indirectly. Most preferably, these agents include insulin-like growth factors-I, insulin-like growth factors-II, platelet dervied growth factors, acidic fibroblast growth factors, basic fibroblast growth factors, transforming growth factors-α, transforming growth factors-β, brain derived neurotrophic factors, ciliary neurotrophic factors, and glial growth factors. Therapeutic agents may also include whole cells or their parts which may be delivered into the lumen of the device. These preferably include Schwann cells, but may also include endothelial cells, fibroblasts, or genetically altered cells or mixtures thereof.

Experimental Models

The device of the present invention was tested for the promotion of in vivo regeneration of peripheral nerves. The primary intention of the experiments was to determine if the presence of all three components of the device was essential for effectively promoting axonal regeneration in a severe nerve injury.

1. Open-Ended Silicone Tubes with and without Guiding Filaments in the Presence or Absence of Growth Factors Prior to surgery, 18 mm Silastic™ tubes (I.D. 1.5 mm) were prepared with or without guiding filaments (four 10-0 monofilament nylon) and filled with test substances.

Experimental groups consisted of:

1. Guiding tubes plus Biomatrix
2. Guiding tubes plus Biomatrix plus filaments
3. Guiding tubes plus Biomatrix plus 0.375 µg PDGF ββ and 0.75 µg IGF-1
4. Guiding tubes plus Biomatrix plus 0.375 µg PDGF ββ and 0.75 µg IGF-1 plus filaments.

The sciatic nerves of rats were sharply transected at mid-thigh and guide tubes containing the test substances with and without guiding filaments were sutured over distances of approximately 2 mm to the end of the nerves. In each experiment, the other end of the guide tube was left open. This model simulates a severe nerve injury in which no contact with the distal end of the nerve is present.

After four weeks, the distance of regeneration of axons within the guide tube was tested in the surviving animals using a functional pinch test. In this test, the guide tube is pinched with fine forceps to mechanically stimulate sensory axons. Testing is initiated at the distal end of the guide tube and advanced proximally until muscular contractions are noted in the lightly anesthetized animal. The distance from the proximal nerve transection point is the parameter measured. For histological analysis, the guide tube containing the regenerated nerve was preserved with a fixative. Cross sections were prepared at a point approximately 7 mm from the transection site. The diameter of the regenerated nerve and the number of myelinated axons observable at this point were used as parameters for comparison.

Figure 3:
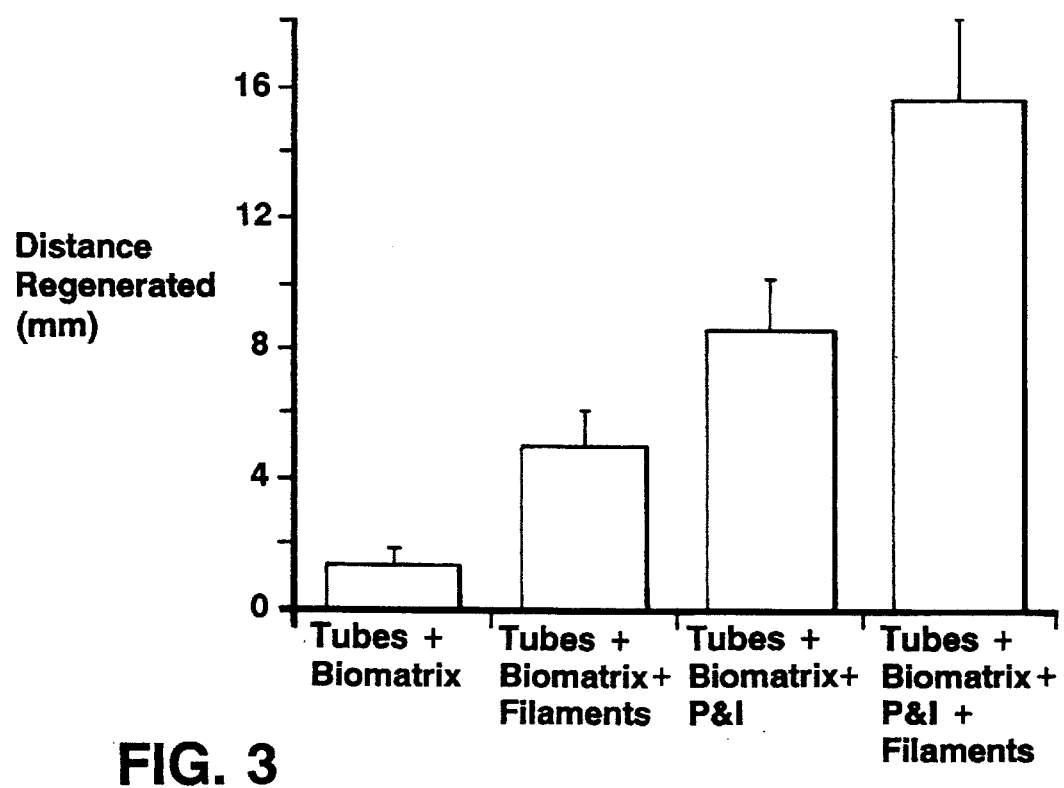
FIG. 3 is a graph illustrating the dependence of the diameter of the regenerated nerve, measured at a distance of 7 mm distal to the transection site, on different components of the device independently and the device as a whole used to stimulate nerve growth. In the graph, "filaments" refers to guiding filaments, "P&I" indicates added platelet derived growth factor ββ and insulin-like growth factor-I.

The measurements of the distance of nerve regeneration are shown in the graph of FIG. 3, and indicate the advantage of having all three components (guide tube, guiding filaments, and growth factors) present in the device.

Figure 2:
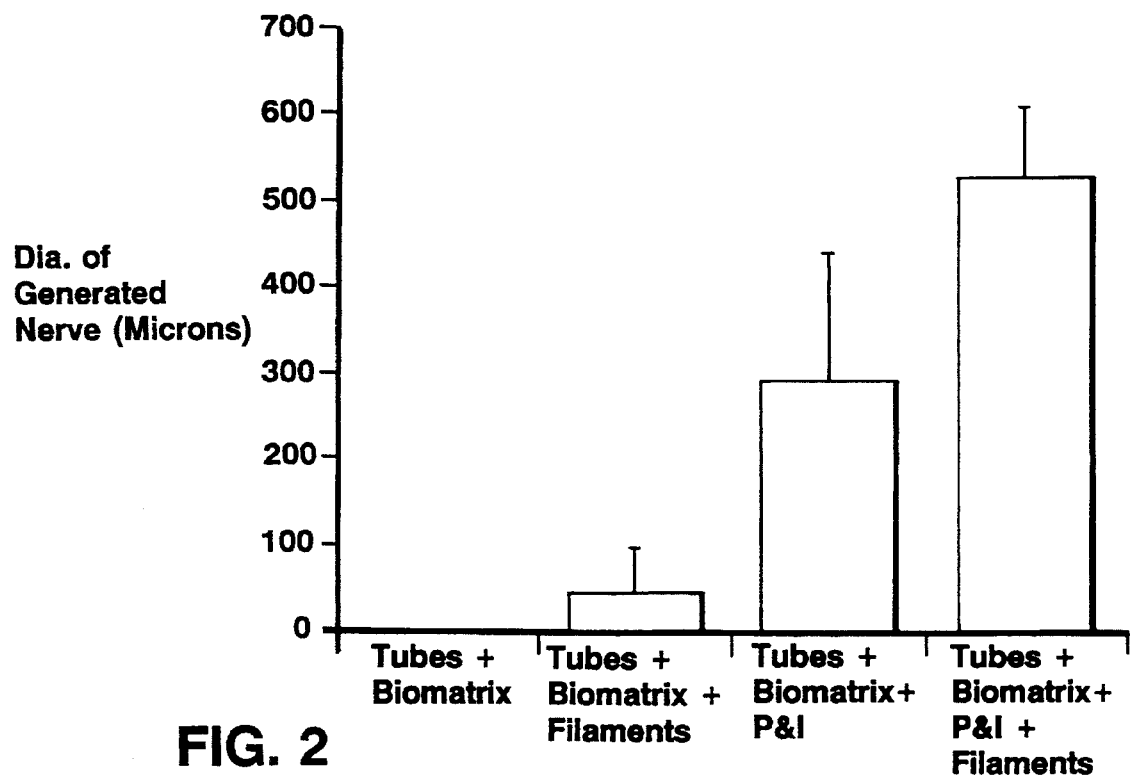
FIG. 2 is a graph illustrating the distance of nerve regeneration with and without guiding filaments. In the graph, "filaments" refers to guiding filaments, "P&I" indicates added platelet derived growth factor ββ and insulin-like growth factor-I.

FIG. 2 shows a plot of the diameter of the regenerated nerve measured at a distance of 7 mm into the guide tube as a function of the presence or absence of one or more components of the device. As shown in FIG. 2, the data exhibit a similar dependence on all three components of the device. No detectable nerve growth was measured at the point sampled in the guide tube with the matrix-forming material alone. The presence of guiding filaments plus the matrix-forming material (no growth factors) induced only very minimal regeneration at the 7 mm measurement point. By far the best results, as assessed by the diameter of the regenerating nerve, were produced by the device which consisted of the guide tube, guiding filaments and growth factors.

Figure 4:
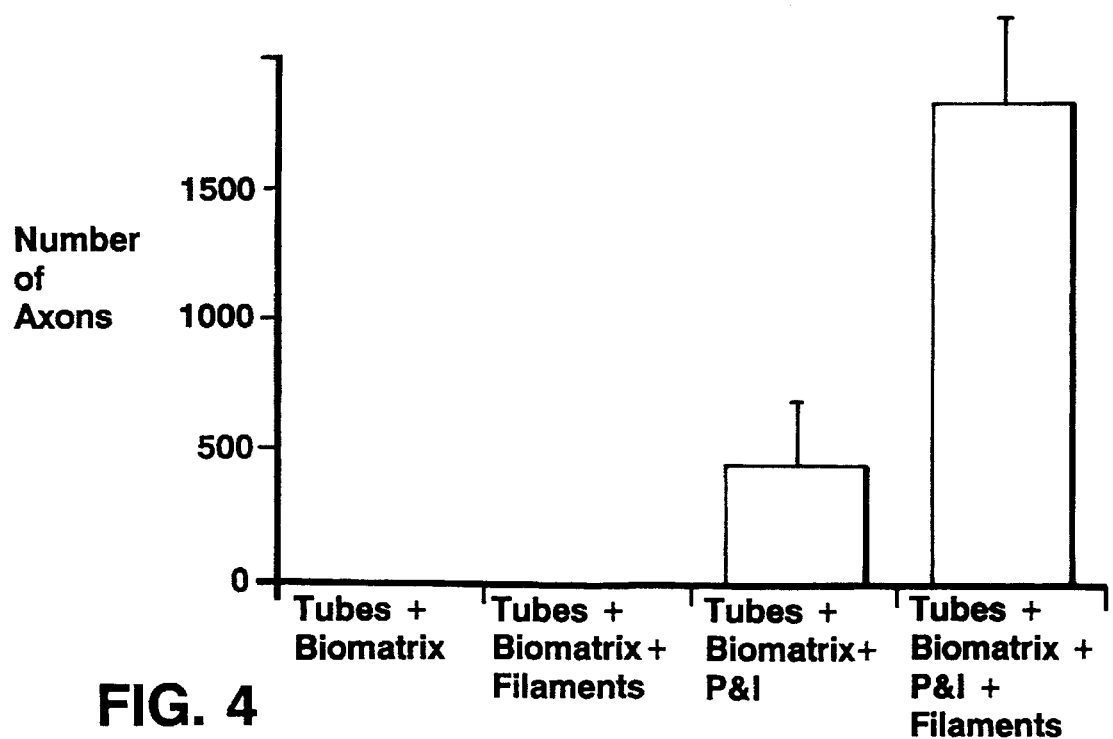
FIG. 4 is a graph illustrating the dependence of the number of regenerated axons, measured at a distance of 7 mm distal to the transection site, on different components of the device independently and the device as a whole used to stimulate nerve growth. Filaments refers to guiding filaments, "P&I" indicates added platelet derived growth factor ββ and insulin-like growth factor-I.

Referring to FIG. 4, treatments using guide tubes comprising either a matrix-forming material alone, or a matrix-forming material in the presence of guiding filaments, resulted in no measured growth of myelinated axons. In contrast, treatments using a device comprising guide tubes, guiding filaments, and matrix containing growth factors, resulted in axon regeneration, with the measured number of axons being increased markedly by the presence of guiding filaments.

Using the severe injury model, the results shown in FIGS. 2-4 demonstrate how the presence of guiding filaments in the guide tube greatly enhances the regeneration of axons, particularly in the presence of added growth factors. The use of guide filaments also resulted in a substantial increase in the number of axons promoted by the addition of growth factors such as PDGF-ββ and IGF-I.

2. Gap Chamber Model of Nerve Repair

Following the gap chamber model of a nerve injury (Lundborg et al., Brain Res. 178: 573–576 (1979); Lundborg et al., J. Hand Surg. 5: 35–38 (1980)), an 8 mm gap was created in the sciatic nerve of rat specimens. The proximal and distal ends of the severed nerve were then inserted 2 mm into a guide tube having an internal diameter of 1.5 mm and a length of 12 mm in a manner similar that illustrated in FIG. 1. The chamber between the severed nerve ends was then filled with a 2% methyl cellulose solution, and experiments were conducted using guide tubes with and without guiding filaments. After a 4 week survival period, the regenerated nerves were evaluated using a pinch test as described above.

Experimental groups consisted of:

1. Tubes plus methyl cellulose matrix
2. Tubes plus methyl cellulose matrix plus guiding filaments
3. Tubes plus methyl cellulose matrix plus guiding filaments plus 0.375 µg PDGF ββ and 0.75 µg IGF-I.

Figure 5:
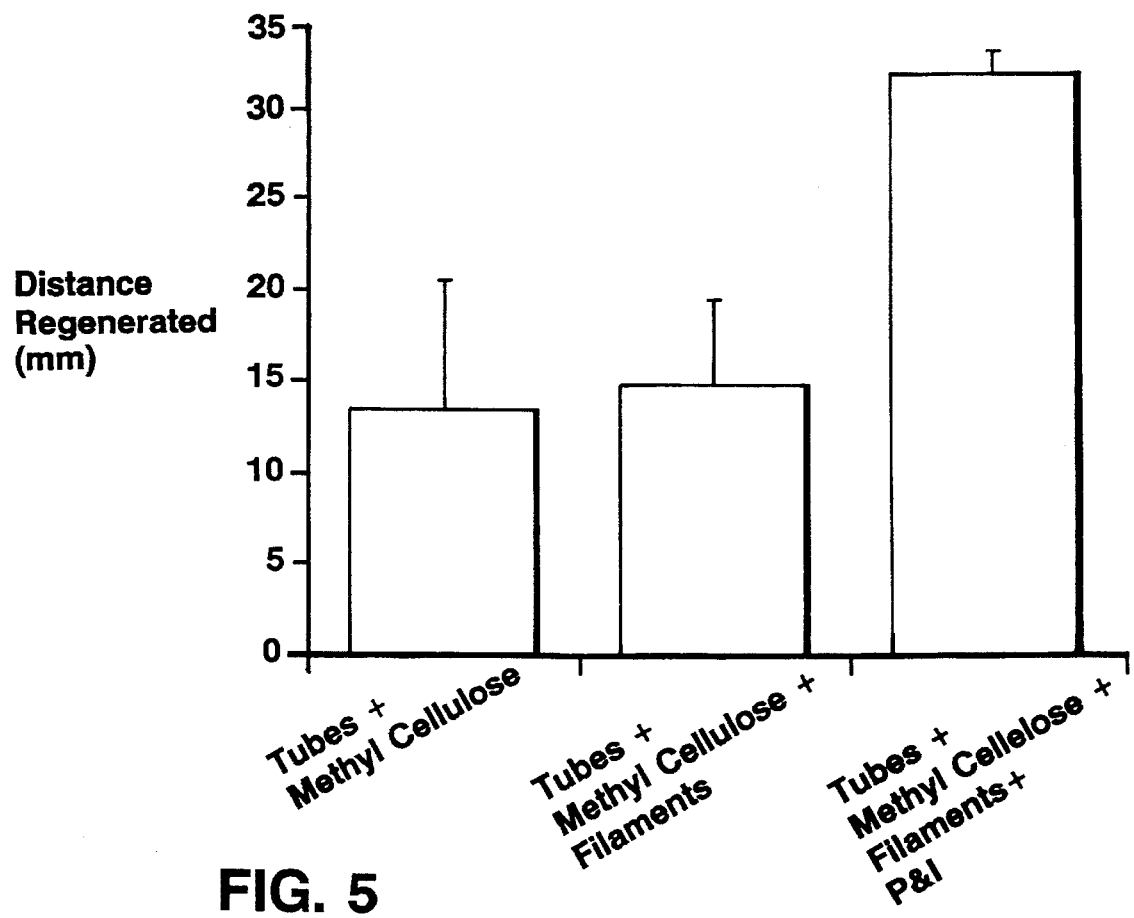
FIG. 5 is a graph illustrating the functional distance of nerve regeneration with and without guide filaments using a 2% methyl cellulose solution as a matrix-forming material.

Referring to FIG. 5, data shown in the graph illustrate how the presence of guiding filaments increases the regeneration of axons into a matrix-forming material (i.e. methyl cellulose) comprising a therapeutic agent. Using a histological analysis, it was possible to determine that in virtually all cases the regenerating nerve was formed around the guiding filaments.

Previous data in the literature has shown the advantage of placing a guide tube containing a therapeutic agent across large defects in injured peripheral nerves in order to enhance axon regeneration. The data presented here demonstrate the advantage of inserting guiding filaments within a guide tube containing a matrix and nerve growth promoting substances as a means of further enhancing the regeneration of axons during peripheral nerve injury repair. The data presented above demonstrate that the presence of all three components of the claimed device, that is a guiding tube, guiding filaments and nerve-growth-stimulating agents, are essential in order to optimize the healing of the damaged nerve.

The foregoing descriptions of preferred embodiments of the present invention have been presented for purposes of illustration and description. It is not intended to be exhaustive or to limit the invention to the precise form disclosed. The embodiments chosen are described in order to best explain the principles of the invention.

What is claimed is:

1. A device for promoting the growth of a nerve in a mammal, comprising:

a polymeric tubular encasing structure for placement over a damaged region of said nerve, said encasing structure having a longitudinal axis;

a therapeutic composition comprising a nerve-growth-stimulating agent suspended or dissolved in a liquid or gel-based matrix-forming material enclosed by said-encasing structure, said matrix-forming material comprising a methyl-cellulose gel and said therapeutic composition stimulating growth of said nerve in said damaged region; and at least one guiding filament disposed in said encasing structure generally parallel to said structure's longitudinal axis to facilitate nerve growth along said axis.

2. A device for promoting the growth of a nerve in a mammal, comprising:

a polymeric encasing structure for placement over a damaged region of said nerve, said encasing structure having a longitudinal axis, a therapeutic composition comprising a nerve-growth-stimulating agent dispersed in a methyl-cellulose gel enclosed by said encasing structure, said therapeutic composition being capable of stimulating growth of said nerve in said damaged region, and at least one guiding filament disposed in said encasing structure generally parallel to its longitudinal axis to facilitate nerve growth in a direction generally parallel to said longitudinal axis.

3. A device for promoting the growth of a nerve in a mammal, comprising:

a tubular polymeric encasing structure for placement over a damaged region of said nerve, said encasing structure having a longitudinal axis, a therapeutic composition comprising a nerve-growth-stimulating agent and a biocompatable liquid solution, said therapeutic composition being capable of stimulating growth of said nerve in said damaged region, and at least one guiding filament disposed in said encasing structure generally parallel to its longitudinal axis to facilitate nerve growth in a direction generally parallel to said longitudinal axis.

4. The device of claim 3, wherein said biocompatable liquid solution is a buffer solution.

* * * * *